(12) United States Patent
Kanegae

(10) Patent No.: US 7,319,234 B2
(45) Date of Patent: Jan. 15, 2008

(54) METHOD AND APPARATUS FOR CORRECTING RADIOGRAPHIC IMAGES

(75) Inventor: Yukio Kanegae, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 11/368,517

(22) Filed: Mar. 7, 2006

(65) Prior Publication Data

US 2006/0210135 A1    Sep. 21, 2006

(30) Foreign Application Priority Data

Mar. 7, 2005   (JP) .............................. 2005-062592

(51) Int. Cl.
   *G03B 42/08*   (2006.01)
(52) U.S. Cl. ...................... 250/587; 250/580; 250/581; 250/582; 250/586
(58) Field of Classification Search ................ 250/580, 250/581, 582, 586, 587
See application file for complete search history.

(56) References Cited

U.S. PATENT DOCUMENTS

| | | | |
|---|---|---|---|
| 5,815,418 A | * | 9/1998 | Dolazza et al. ............... 702/86 |
| 5,832,055 A | * | 11/1998 | Dewaele ...................... 378/62 |
| 6,350,985 B1 | * | 2/2002 | Rodricks et al. ......... 250/252.1 |

FOREIGN PATENT DOCUMENTS

| | | |
|---|---|---|
| JP | 2000-13599 A | 1/2000 |
| JP | 2001-166404 A | 6/2001 |

* cited by examiner

*Primary Examiner*—David Porta
*Assistant Examiner*—Casey Bryant
(74) *Attorney, Agent, or Firm*—Sughrue Mion Pllc.

(57) ABSTRACT

Structural noise is accurately removed by a radiographic image correcting apparatus. A correction image data set, generated from a reference image data set obtained from a stimulable phosphor sheet onto which radiation has been uniformly irradiated, that includes at least four times the amount of structural noise compared to quantum noise, is recorded in a memory means. A correcting means corrects a radiographic image data set, employing the correction image data set recorded in the memory means.

12 Claims, 3 Drawing Sheets

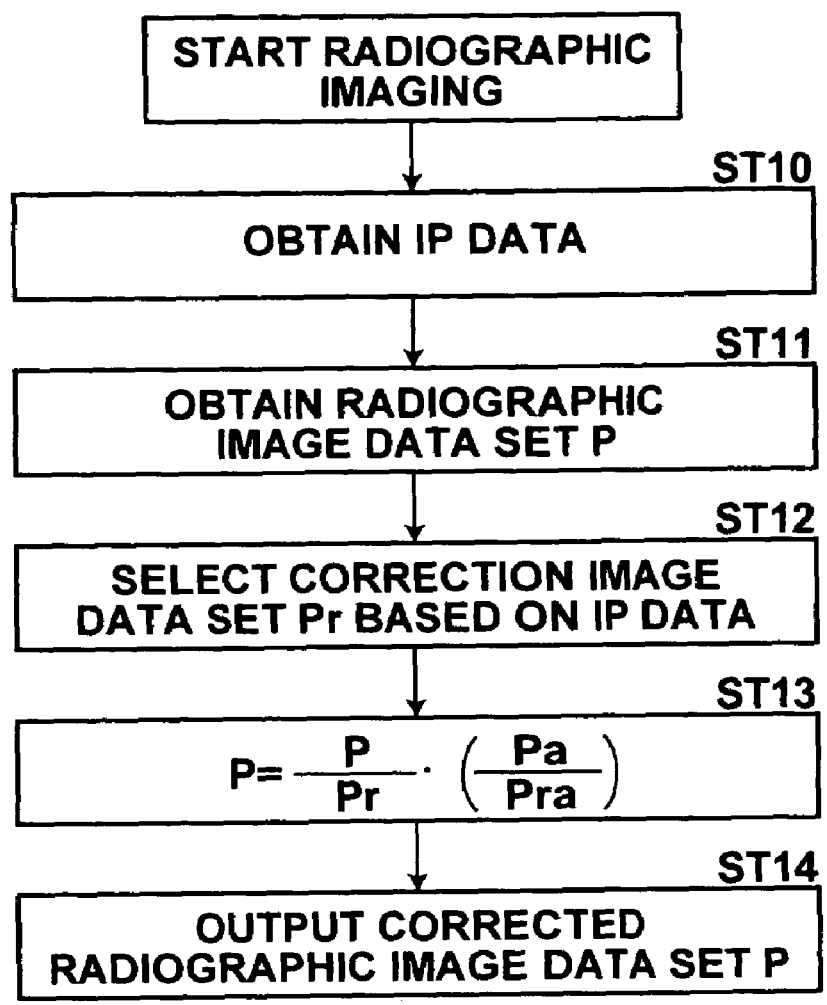

METHOD AND APPARATUS FOR CORRECTING RADIOGRAPHIC IMAGES

BACKGROUND OF THE INVENTION

1. Field of the Invention

The present invention relates to a radiographic image correcting apparatus, for removing noise from radiographic image data sets, which are obtained from stimulable phosphor sheets.

2. Description of the Related Art

When certain types of phosphors are irradiated with radiation (X-rays, α-rays, β-rays, γ-rays, electron beams, ultraviolet rays, and the like), a portion of the radiation energy accumulates within the phosphors. When excitation light, such as visible light, is irradiated onto the phosphors, the phosphors emit stimulated phosphorescence corresponding to the energy accumulated therein. Phosphors having this property are referred to as stimulable phosphors. Image readout apparatuses that utilize these stimulable phosphors have been proposed. Radiographic image information of a subject, such as a human body, is temporarily recorded in a stimulable phosphor sheet. Then, excitation light is irradiated onto the stimulable phosphor sheet to cause stimulated phosphorescence to be emitted. The image readout apparatuses photoelectrically read out the stimulated phosphorescence to obtain image signals.

There is a problem that noise generated due to the stimulable phosphor sheet is unavoidable in the radiographic image information obtained by the image readout apparatuses. The noise generated due to the stimulable phosphor sheet includes: X-ray quantum noise, light quantum noise, and fixed noise (Refer to Eiji Ogawa et al., "Quantitative Analysis of Imaging Performance for Computed Radiography Systems", SPIE, Vol. 2432, pp. 421-431, 1995).

Here, the X-ray quantum noise and the light quantum noise are random noise that depends on the X-ray dosage and the amount of light emission accompanying X-ray irradiation. The X-ray quantum noise and the light quantum noise have an inverse proportionate relationship with the X-ray dosage. That is, X-ray quantum noise and light quantum noise are prevalent at low X-ray dosage regions, and minimal at high X-ray dosage regions. On the other hand, the fixed noise is mainly unique noise inherent to the sheet. The fixed noise is caused by differences in the amounts of emitted light at different positions on the surface of the sheet. The fixed noise influences image quality at the practical dosage regions and at high dosage regions. Fixed noise having comparatively long periods (low frequencies) are referred to as "sheet irregularities". However, the frequency of the fixed noise is not limited to low frequencies. Fixed noise having high frequencies (for example, 0.5 c/mm to the Nyquist frequency) also exists. The fixed noise having the range of low to high frequencies is collectively referred to as "structural noise" (or structural mottle). Each sheet possesses a different noise pattern, and the noise appears as graininess in images.

Japanese Unexamined Patent Publication No. 2000-013599 discloses a method for removing the structural noise. In this method, first, a solid image is obtained from a stimulable phosphor sheet, which has undergone solid exposure (uniform exposure). Then, radiographic images are corrected based on the solid image.

Japanese Unexamined Patent Publication No. 2001-166404 discloses another method for removing the structural noise. In this method, the relationship between the amount of excitation light, which is transmitted through a stimulable phosphor sheet when the excitation light is irradiated thereon, and the amount of stimulated phosphorescence emitted by the stimulable phosphor sheet when the excitation light is irradiated thereon is obtained. Then, actual images are corrected, based on this relationship.

However, in the method disclosed in Japanese Unexamined Patent Publication No. 2000-013599, the solid image, which is the reference for correction, includes both structural noise and quantum noise. Therefore, there is a problem that the accuracy in correction of the structural noise is poor.

In the method disclosed in Japanese Unexamined Patent Publication No. 2001-166404, a photodetecting means for detecting the amount of excitation light which is transmitted through the stimulable phosphor sheet is necessary. Therefore, there is a problem that the apparatus becomes large.

SUMMARY OF THE INVENTION

The present invention has been developed in view of the aforementioned points. It is an object of the present invention to provide a radiographic image correcting apparatus which is capable of accurately removing structural noise.

The radiographic image correcting apparatus of the present invention is that which corrects a radiographic image data set obtained by detecting stimulated phosphorescence emitted by a stimulable phosphor sheet, on which a radiographic image is recorded, when the stimulable phosphor sheet is irradiated with excitation light, comprising:

memory means, in which a correction image data set of a reference image, obtained from the stimulable phosphor sheet onto which radiation has been uniformly irradiated, that includes at least four times the amount of structural noise compared to quantum noise, is recorded; and correcting means, for correcting the radiographic image data set employing the correction image data set recorded in the memory means.

Here, the "quantum noise" refers to random noise that depends on fluctuations in amounts of stimulated phosphorescence emitted by the stimulable phosphor sheet, due to fluctuations in the dosages of radiation which is irradiated. The "structural noise" refers to noise unique to the stimulable phosphor sheet, due to differences in the amounts of emitted light at different positions on the surface of the sheet.

Note that the correction image data set may be generated from a reference image data set obtained from the stimulable phosphor sheet, onto which high dosage radiation is uniformly irradiated. Alternatively, the correction image data set may be generated by averaging a plurality of reference image data sets. Here, "averaging a plurality of reference image data sets" refers to averaging signals of corresponding signals within the plurality of reference image data sets. The term "high dosage radiation" refers to radiation at dosages of 100 mR or greater, and preferably 150 mR or greater. The term "plurality of reference image data sets" refers to two or more reference image data sets, and preferably ten or more reference image data sets.

Further, the correction image data set may be processed by a low pass filter.

The correcting method employed by the correcting means may be any method, as long as it employs the correction image data set to correct the radiographic image data set. For example, the correction may be performed by normalizing the radiographic image data set employing the correction image data set. Alternatively, the correction may be performed by subtracting the correction image data set from the radiographic image data set.

Further, a marker may be provided at a predetermined position of the stimulable phosphor sheet. In this case, the correcting means matches the positions of the marker included in the radiographic image data set and the marker in the correction image data set when performing correction of the radiographic image data set.

The radiographic image correcting apparatus of the present invention comprises: the memory means, in which a correction image data set of a reference image, obtained from the stimulable phosphor sheet onto which radiation has been uniformly irradiated, that includes at least four times the amount of structural noise compared to quantum noise, is recorded; and the correcting means, for correcting the radiographic image data set employing the correction image data set recorded in the memory means. Therefore, the radiographic image data set is corrected employing the correction image data set, in which structural noise is dominant. Accordingly, the structural noise included in the radiographic image data set can be positively corrected, and deterioration of image quality of the corrected radiographic image data set, due to quantum noise (random noise) included in the correction image data set, can be prevented.

Note that the correction image data set may be generated from a reference image data set obtained from the stimulable phosphor sheet, onto which high dosage radiation is uniformly irradiated. Generally, structural noise becomes dominant as the dosage increases Therefore, in this case, correction of the radiographic image data set employing a correction image data set having structural noise as dominant noise is enabled. Accordingly, the structural noise included in the radiographic image data set can be positively corrected, and deterioration of image quality of the corrected radiographic image data set, due to quantum noise (random noise) included in the correction image data set, can be prevented.

Alternatively, the correction image data set may be generated by averaging a plurality of reference image data sets. In this case, the structural noise included in the correction image data set can be maintained at a constant level, while quantum noise is reduced. Therefore, generation of a correction image data set having structural noise as dominant noise is enabled. Accordingly, the structural noise included in the radiographic image data set can be positively corrected, and deterioration of image quality of the corrected radiographic image data set, due to quantum noise (random noise) included in the correction image data set, can be prevented.

Further, in the case that high frequency components are removed from the correction image data set, differences in signal levels between adjacent pixels can be reduced. Therefore, even if positional misalignment occurs between the radiographic image data set and the correction image data set, the deterioration in correction accuracy can be minimized.

A configuration may be adopted, wherein the correcting means performs correction by normalizing the radiographic image data set, employing the correction image data set. In this case, correction of the radiographic image data set can be performed corresponding to the radiation dosage utilized when obtaining the radiographic image data set.

A configuration may be adopted, wherein a marker is provided at a predetermined position of the stimulable phosphor sheet; and the correcting means matches the positions of the marker included in the radiographic image data set and the marker in the correction image data set when performing correction of the radiographic image data set. In this case, positional misalignment between the radiographic image data set and the correction image data set can be prevented. Accordingly, structural noise can be positively corrected.

BRIEF DESCRIPTION OF THE DRAWINGS

FIGS. 1A and 1B illustrate an image readout apparatus, in which a radiographic image correcting apparatus of the present invention is incorporated, Wherein: FIG. 1A is a perspective view of the image readout apparatus; and FIG. 1B is a sectional view taken along line I-I of FIG. 1A.

FIG. 4 is a flow chart that illustrates an example of the operation of the radiographic image correcting apparatus of the present invention.

DESCRIPTION OF THE PREFERRED EMBODIMENTS

Figure 1A:
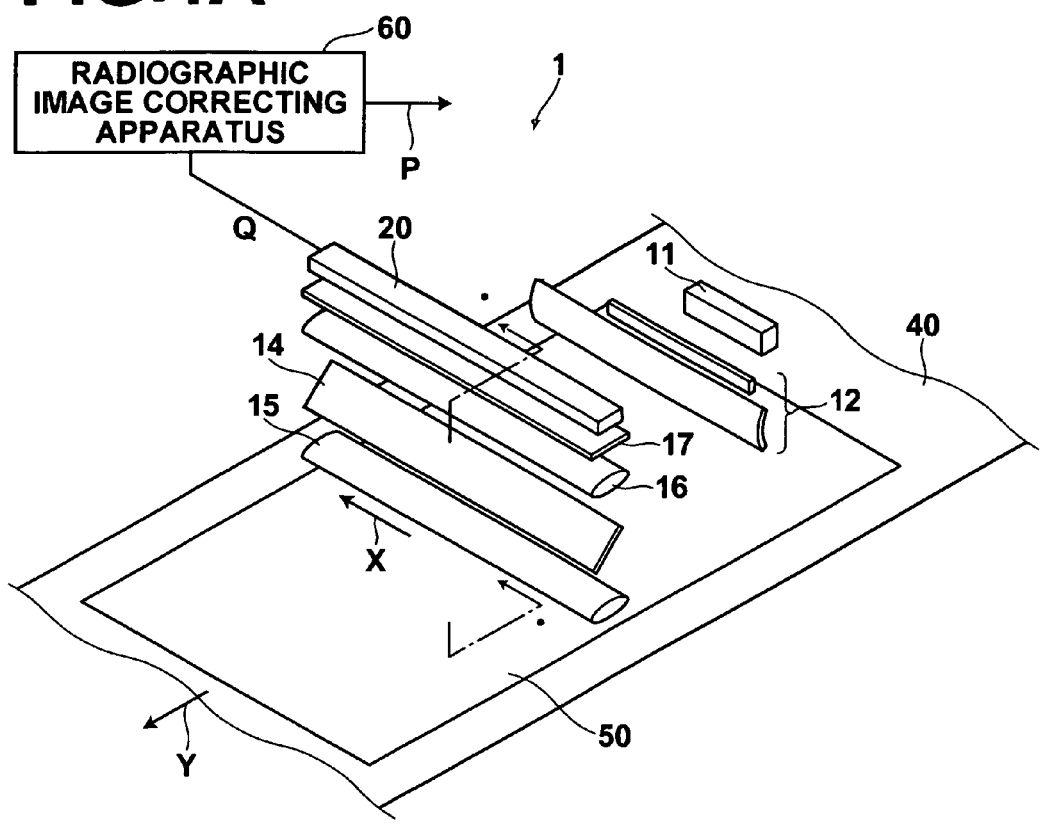
Figure 1B:
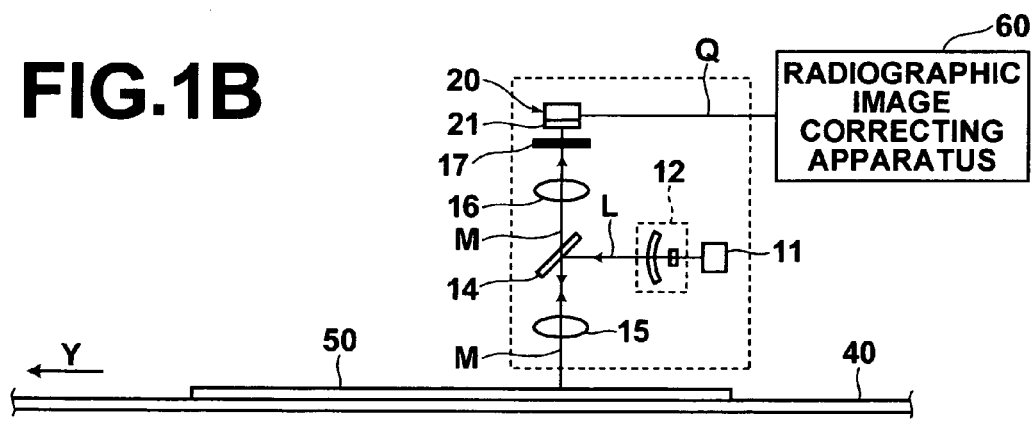

Hereinafter, an embodiment of the radiographic image correcting apparatus of the present invention will be described in detail with reference to the attached drawings. FIGS. 1A and 1B illustrate an image readout apparatus 1, in which a radiographic image correcting apparatus 60 is incorporated. Note that FIG. 1A is a perspective view of the image readout apparatus, and FIG. 1B is a sectional view taken along line I-I of FIG. 1A.

The image readout apparatus 1 illustrated in FIGS. 1A and 1B comprises: a scanning belt 40, on which a stimulable phosphor sheet 50 (hereinafter, simply referred to as "sheet 50") having radiographic image data recorded therein is placed and conveyed in the direction of arrow Y; an excitation light source 11, for emitting a linear secondary excitation light beam L (hereinafter, simply referred to as "excitation light beam") having a line width of approximately 100 μm onto the surface of the sheet 50 parallel thereto; a line sensor 20 comprising a great number of photoelectric conversion elements 21, for detecting stimulated phosphorescence M, which is emitted by the sheet 50 when the sheet 50 is irradiated by the excitation light emitted by the excitation light source 11; and the radiographic image correcting apparatus 60, for sequentially reading out the signals output from each of the photoelectric conversion elements 21 of the line sensor 20 corresponding to the movement of the sheet 50, to obtain an image signal S1 that represents the radiographic image data recorded in the sheet 50.

An optical system 12, comprising: a collimating lens, for collimating the linear excitation light beam L emitted from the excitation light source 11; and a toric lens, for spreading the excitation light beam L unidirectionally; is provided between the excitation light source 11 and the sheet 50. A dichroic mirror 14, for reflecting the light that propagates through the optical system 12 toward the sheet 50; and a gradient index lens array 15 (an array constituted by a great number of gradient index lenses, hereinafter referred to as a "first Selfoc lens array); are provided between the optical system 12 and the sheet 50.

The first Selfoc lens array 15 is configured to collimate the stimulated phosphorescence M, corresponding to the radiographic image data, emitted from the sheet 50 due to irradiation of the linear excitation light beam L, and to cause the stimulated phosphorescence M to propagate toward the dichroic mirror 14. The dichroic mirror 14 is configured to transmit the stimulated phosphorescence M emitted from the sheet 50 therethrough.

Further, a second Selfoc lens array 16, for focusing the stimulated phosphorescence M, which is transmitted through the dichroic mirror 14, onto the light receiving surfaces of each of the photoelectric conversion elements 21, and an excitation light cutoff filter 17, for cutting off the excitation light beam L, which is reflected by the surface of the sheet 50 and is included in the stimulated phosphorescence M that passes through the second Selfoc lens array 16, are provided between the dichroic mirror 14 and the line sensor 30.

Next the operation of the image readout apparatus 1 will be described. First, the scanning belt 40 moves in the direction of arrow Y. Thereby, the sheet 50, which is placed on the scanning belt 40 and on which radiographic image data is recorded, is conveyed in the direction of arrow Y. Meanwhile, the excitation light beam L, which extends in the direction of arrow X, is emitted from the excitation light source 11 substantially parallel to the surface of the sheet 50. The excitation light beam L is focused on the sheet 50, via the optical system 12, the dichroic mirror 14, and the first Selfoc lens array.

The linear excitation light beam L that enters the sheet 50 stimulates the stimulable phosphors at its focal region. In addition, the linear excitation light beam L enters the sheet 50 beyond its focal region and is dispersed into the vicinity thereof, thereby stimulating phosphors in the vicinity of the focal region thereof. As a result, stimulated phosphorescence M, of intensities corresponding to the recorded radiographic image data, is emitted from the focal region of the excitation light beam L and the vicinity thereof within the sheet 50.

The stimulated phosphorescence M emitted from the sheet 50 is collimated by the first Selfoc lens array, passes through the dichroic mirror 14, and is focused onto the light receiving surfaces of each of the photoelectric conversion elements 21 of the line sensor 20 by the second Selfoc lens array 16. At this time, the excitation light beam L, which is reflected by the surface of the sheet 50 and which is included in the stimulated phosphorescence M that passes through the second Selfoc lens array 16, is cut off by the excitation light cutoff filter 17.

Each of the photoelectric conversion elements 21 of the line sensor photoelectrically convert the stimulated phosphorescence M focused thereon, and outputs signals Q to the radiographic image correcting apparatus 60. The signals Q, which are input to the radiographic image correcting apparatus 60, are A/D converted and recorded, corresponding to the position of the sheet 50. Thereby, a radiographic image data set P that represents the radiographic image recorded on the sheet 50 is obtained.

Figure 2:
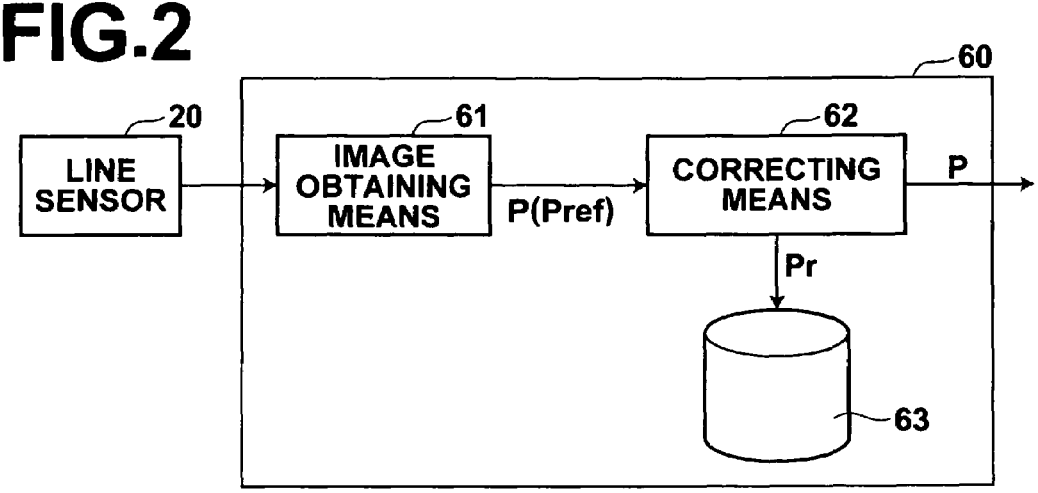
FIG. 2 is a block diagram illustrating a preferred embodiment of the radiographic image correcting apparatus of the present invention.

FIG. 2 is a block diagram illustrating a preferred embodiment of the radiographic image correcting apparatus of the present invention. The radiographic image correcting apparatus 60 illustrated in FIG. 2 comprises: an image obtaining means 61, for obtaining radiographic image data sets P and a reference image data set Pref, based on signals obtained from the line sensor 20; a memory means 63, in which a correction image data set Pr of the reference image Pref, obtained from the sheet 50 onto which radiation has been uniformly irradiated, that includes at least four times the amount of structural noise compared to quantum noise, is recorded; and a correcting means 62, for correcting the radiographic image data set P obtained by the image obtaining means 61 employing the correction image data set Pr recorded in the memory means 63.

Here, the radiographic image data set P obtained by the image obtaining means 61 and the reference image data set Pref each include a marker, which is provided at a predetermined position of the sheet 50. Specifically, the sheet 50 comprises a marker formed by fluorescent material or a cutout, and an image portion that represents the marker is included in the radiographic image data set P and the reference image data set Pref. As will be described later, the marker is used as a reference when positioning the radiographic image data set P and the reference image data set Pref.

A plurality of unique ID's each corresponding to a sheet 50, and a plurality of correction image data sets Pr are recorded in the memory means 63, correlated with each other. The correcting means 62 performs correction of the radiographic image data sets P employing the correction image data set Pr corresponding to each sheet 50.

Figure 3:
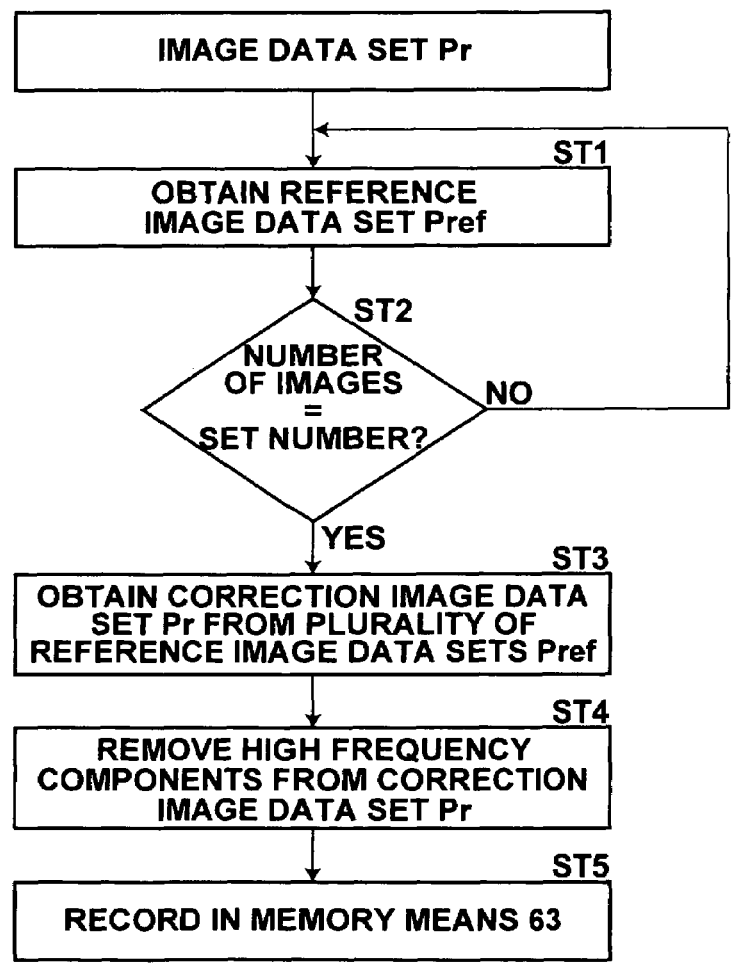
FIG. 3 is a flow chart that illustrates an example of a process by which a correction image data set Pr is generated.

As described above, the correction image data sets Pr include at least four times the amount of structural noise compared to quantum noise, and are generated from reference image data sets Pref, obtained from sheets 50, on which radiation has been uniformly irradiated. FIG. 3 is a flow chart that illustrates an example of a process by which a correction image data set Pr is generated from a reference image data set Pref. A description of the process by which the correction image data set Pr is generated will be described with reference to FIG. 3.

First, a sheet 50, on which radiation has been uniformly irradiated, is placed on the scanning belt 40 (refer to FIG. 1). At this time, the radiation dosage may be as high as 150 mR, or as low as 25 mR. Reference image data sets Pref are obtained from the sheet 50 (step ST1). Next, it is judged whether a set number of reference image data sets Pref have been obtained (step ST2), and obtainment of the reference image data sets Pref is repeated until the set number is reached (steps ST1 and ST2). Thereafter, the correcting means 62 calculates the average values of each pixel of each of the plurality of reference image data sets Pref, and one correction image data set Pr is obtained (step ST3).

Generally, the amount of structural noise is proportional to the radiation dosage, and the amount of quantum noise is proportional to the square root of the radiation dosage. Accordingly, quantum noise becomes dominant when the radiation dosage is low, and structural noise becomes dominant when the radiation dosage is high. Specifically, a reference image data set Pref obtained when radiation at a dosage of 7 mR is irradiated, for example, includes approximately the same levels of structural noise and quantum noise. On the other hand, if the radiation dosage is as high as 150 mR, the amount of structural noise included in a reference image data set Pref obtained thereby is approximately five times the amount of quantum noise.

Meanwhile, in the case that the radiation dosage is not high, for example, 25 mR, a reference image data set Pref obtained thereby includes less than four times the amount of structural noise with respect to the amount of quantum noise. However, a correction image data set Pr that includes at least four times the amount of structural noise with respect to the amount of quantum noise can be obtained, by averaging a plurality of reference image data sets Pref. That is, structural noise is dependent on position, and therefore is not attenuated even when averaged. On the other hand, quantum noise is random noise that depends on the X-ray dosage and the amount of light emission from the sheet 50 accompanying X-ray irradiation. Therefore, when the plurality of reference image data sets Pref is averaged, the amount of quantum noise decreases, proportionate to the square root of the number of reference image data sets Pref. That is, when the plurality of reference image data sets Pref is averaged, the structural noise remains constant while the quantum noise is attenuated. As a result, the percentage of structural noise becomes greater than the percentage of quantum noise.

The number of reference image data sets Pref to be obtained is set to 10, for example, and the correction image data set Pr that includes at least four times the amount of structural noise compared to quantum noise is obtained by averaging the 10 reference image data sets Pref. Thereby, even in the case that a reference image data set Pref includes quantum noise, it is possible to generate a correction image data set Pr, in which structural noise is dominant, from the reference image data set Pref. Therefore, the necessity to irradiate high dosage radiation onto the sheet 50 is obviated.

Note that in the case that the radiation dosage is high, the number of reference image data sets Pref to be obtained may be set to one. A case has been described above, in which the radiation dosage employed during generation of the correction image data set Pr is not high. Alternatively, the correction image data set Pr may be obtained by averaging a plurality of reference image data sets Pref, which have been obtained by irradiating high dosage radiation. In this case, reference image data sets Pref, in which the amounts of quantum noise are low, are averaged, further reducing the amount of quantum noise. Therefore, a radiographic image data set P can be corrected with a correction image data set Pr that represents structural noise.

Further, the correcting means 62 administers a low pass filter process on the obtained correction image data set Pr (step ST4), to remove high frequency components from the correction image data set Pr. The correction image data set Pr is recorded in the memory means 63, correlated with the ID of the sheet 50 (step ST5).

A smoothing operation, by which the high frequency components are removed form the correction image data set Pr, is performed in this manner. Thereby, when the correcting means 62 corrects the radiographic image data set P, deterioration of correction accuracy can be minimized, even if the pixel positions of the radiographic image data set P and the correction image data set Pr are misaligned. That is, structural noise has different noise properties at each position on the sheet 50, and there are cases in which correction cannot be performed accurately, if the positions of the radiographic image data set P and the correction image data set Pr are misaligned. Variance of signal values of adjacent pixels within the correction image data set Pr can be reduced, by removing the high frequency components therefrom. Thereby, the deterioration in correction accuracy can be minimized.

FIG. 4 is a flow chart that illustrates an example of the operation of the radiographic image correcting apparatus 60 of the present invention. The example of the operation of the radiographic image correcting apparatus 60 will be described with reference to FIGS. 1 through 4. First, the ID data of the sheet 50, from which the radiographic image data set P is to be read out, is obtained (step ST10). The ID data may be input to the correcting means 62 by an operator of the apparatus, or may be automatically read out from the sheet 50. Next, the radiographic image data set P is obtained from the sheet 50 by the image obtaining means 61, and transmitted to the correcting means 62 (step ST11).

The correcting means selects a correction image data set Pr from among the plurality of correction image data sets Pr recorded in the memory means 63, based on the obtained ID data (step ST12). The radiographic image data set P is corrected, employing the selected correction image data set Pr (step ST13). Specifically, first, the positions of the markers included in the radiographic image data set P and the correction image data set Pr are matched. Thereby, structural noise, which is dependent on the position within the sheet 50, can be positively removed.

Next, an average signal value Pa of each of the pixels that constitute the radiographic image data set P is calculated, and an average signal value Pra of each of the pixels that constitute the correction image data set Pr is calculated. Thereafter, a normalizing process is administered with respect to each pixel that constitutes the radiographic image data set P, and a corrected radiographic image data set $P=(P/Pr)\times(Pa/Pra)$ is calculated. By performing correction by the normalizing processes in this manner, signal levels can be adjusted to those of the structural noise within the radiographic image data set P, even if the radiation dosage employed when obtaining the radiographic image data set P is different from that employed when obtaining the reference image data set Pref. The corrected radiographic image data set P is output from the correcting means 62 (step ST14).

The embodiment described above comprises: the memory means 63, in which the correction image data set Pr, obtained from the sheet 50 onto which radiation has been uniformly irradiated, that includes at least four times the amount of structural noise compared to quantum noise, is recorded; and the correcting means 62, for correcting the radiographic image data set P employing the correction image data set Pr recorded in the memory means 63. Therefore, the structural noise included in the radiographic image data set can be positively corrected, and deterioration of image quality of the corrected radiographic image data set, due to quantum noise (random noise) included in the correction image data set, can be prevented.

In the case that a correction image data set, in which random noise (quantum noise) is dominant, is employed to correct the radiographic image data set P, there is a problem that the image quality of the resulting corrected radiographic image data set deteriorates due to the random noise. At the same time, there is a problem that structural noise cannot be effectively removed from the radiographic image data set P, by using the correction image data set Pr, in which the percentage of structural noise (fixed noise) is low.

It was discovered that it is necessary for the correction image data set to include at least four times (preferably at least five times) the amount of structural noise compared to quantum noise in order to positively remove the structural noise from the radiographic image data set P, while preventing the deterioration in image quality due to random noise. That is, deterioration of image quality due to random noise can be achieved, by setting the ratio of random noise with respect to structural noise to be ¼ or less. At the same time, by setting the amount of structural noise to be at least four times the amount of quantum noise, that is, dominant within the correction image data set Pr, structural noise can be positively removed from the radiographic image data set P.

Note that the correction image data set Pr may be generated from a reference image data set Pref obtained from a sheet 50, onto which high dosage radiation is uniformly irradiated. Generally, structural noise becomes dominant proportionate to the radiation dosage, and therefore, in this case, structural noise becomes dominant in the correction image data set Pr. By employing the correction image data set Pr to correct the radiographic image data set P, structural noise can be removed efficiently.

Alternatively, the correction image data set Pr may be generated by averaging a plurality of image data sets obtained from the sheet 50, on which radiation has been uniformly irradiated. In this case, the amount of quantum noise included in the correction image data set Pr is decreased. Therefore, a correction image data set Pr, in which structural noise is dominant, can be employed to correct the radiographic image data set P. Accordingly, structural noise can be removed efficiently from the radiographic image data set P.

Further, in the case that high frequency components are removed from the correction image data set Pr, differences in signal levels between adjacent pixels can be reduced. Therefore, even if positional misalignment occurs between the radiographic image data set P and the correction image data set Pr, the deterioration in correction accuracy can be minimized.

In addition, the correcting means 62 of FIG. 2 performs correction by normalizing the radiographic image data set employing the correction image data set. Therefore, correction of the radiographic image data set, corresponding to the radiation dosage utilized when obtaining the radiographic image data set, can be performed.

A configuration has been adopted, wherein a marker is provided at a predetermined position of the sheet 50; and the correcting means 62 matches the positions of the marker included in the radiographic image data set P and the marker in the correction image data set Pr when performing correction of the radiographic image data set. Therefore, positional misalignment between the radiographic image data set and the correction image data set can be prevented. Accordingly, structural noise can be accurately removed.

The markers are utilized (the markers are not strictly necessary, and any other positioning means may be employed) to positionally match the images prior to averaging the plurality of reference images. Therefore, structural noise images can be generated, without losing the high frequency components included in the reference images. The structural noise images are employed to correct the radiographic images, and positional matching is performed at this time as well. Accordingly, the cutoff frequency of the lowpass filter can be set to higher frequencies, and structural noise of higher frequencies can also be removed thereby.

The present invention is not limited to the embodiment described above. Various changes and modifications are possible, as long as they do not stray from the spirit of the invention. For example, a case has been described in which the low pass filter process is administered on the correction image data set Pr. However, the correction image data set Pr may be employed to correct the radiographic image data set P, without removing the high frequency components therefrom.

What is claimed is:

1. A radiographic image correcting apparatus, for correcting a radiographic image data set obtained by detecting stimulated phosphorescence emitted by a stimulable phosphor sheet, on which a radiographic image is recorded, when the stimulable phosphor sheet is irradiated with excitation light, comprising:
   memory means, in which a correction image data set of a reference image, obtained from the stimulable phosphor sheet onto which radiation has been uniformly irradiated, that includes at least four times the amount of structural noise compared to quantum noise, is recorded; and
   correcting means, for correcting the radiographic image data set employing the correction image data set recorded in the memory means.

2. A radiographic image correcting apparatus as defined in claim 1, wherein:
   the correction image data set of the reference image is generated from the stimulable phosphor sheet, on which high dosage radiation has been uniformly irradiated.

3. A radiographic image correcting apparatus as defined in claim 1, wherein:
   the correction image data set of the reference image is generated by averaging a plurality of the reference images.

4. A radiographic image correcting apparatus as defined in claim 1, wherein:
   the correction image data set is processed with a low pass filter.

5. A radiographic image correcting apparatus as defined in claim 1, wherein:
   the correcting means corrects the radiographic image data set by normalizing the radiographic image data set, employing the correction image data set.

6. A radiographic image correcting apparatus as defined in claim 1, wherein:
   a marker is provided at a predetermined position of the stimulable phosphor sheet; and
   the correcting means matches the positions of the marker included in the radiographic image data set and the marker in the correction image data set when performing correction of the radiographic image data set.

7. A radiographic image correcting method for correcting a radiographic image data set obtained by detecting stimulated phosphorescence emitted by a stimulable phosphor sheet, on which a radiographic image is recorded, when the stimulable phosphor sheet is irradiated with excitation light, comprising the steps of:
   recording a correction image data set of a reference image, obtained from the stimulable phosphor sheet onto which radiation has been uniformly irradiated, that includes at least four times the amount of structural noise compared to quantum noise; and
   correcting the radiographic image data set employing the recorded correction image data set.

8. A radiographic image correcting method as defined in claim 7, wherein:
   the correction image data set of the reference image is generated from the stimulable phosphor sheet, on which high dosage radiation has been uniformly irradiated.

9. A radiographic image correcting method as defined in claim 7, wherein:
   the correction image data set of the reference image is generated by averaging a plurality of the reference images.

10. A radiographic image correcting method as defined in claim 7, wherein:
    the correction image data set is processed with a low pass filter.

11. A radiographic image correcting method as defined in claim 7, wherein:
    correction of the the radiographic image data set performed by normalizing the radiographic image data set, employing the correction image data set.

12. A radiographic image correcting method as defined in claim 7, wherein:
    a marker is provided at a predetermined position of the stimulable phosphor sheet; and
    the positions of the marker included in the radiographic image data set and the marker in the correction image data set are matched when performing correction of the radiographic image data set.

* * * * *